United States Patent [19]

Jarolics

[11] Patent Number: 5,413,001

[45] Date of Patent: May 9, 1995

[54] METHOD AND APPARATUS FOR SAMPLING GAS FROM A HOT DUST-FILLED GAS STREAM

[75] Inventor: Gyula Jarolics, Valby, Denmark

[73] Assignee: FLS Automation A/S, Denmark

[21] Appl. No.: 101,383

[22] Filed: Jul. 19, 1993

[30] Foreign Application Priority Data

Jul. 21, 1992 [DK] Denmark .............. 0936/92

[51] Int. Cl.$^6$ .............................................. G01N 1/14
[52] U.S. Cl. ................................. 73/863.83; 73/863.23
[58] Field of Search ......... 73/863.83, 863.23–863.25, 73/863.11; 356/438–440; 55/270; 15/104.095, 104, 104.15, 104.16

[56] References Cited

U.S. PATENT DOCUMENTS

| | | | |
|---|---|---|---|
| 3,520,015 | 7/1970 | Deynat | 15/104.095 |
| 4,666,530 | 5/1987 | Houser | 15/104.095 |
| 5,039,322 | 8/1991 | Holzl | 73/863.24 |
| 5,237,881 | 8/1993 | Ross | 73/863.23 |

FOREIGN PATENT DOCUMENTS

| | | |
|---|---|---|
| 162800 | 12/1991 | Denmark . |
| 1815045 | 6/1970 | Germany . |
| 1813877 | 7/1970 | Germany . |
| 2603948 | 9/1976 | Germany . |
| 2224955 | 7/1981 | Germany . |
| 3327180 | 2/1985 | Germany . |
| 1525336 | 9/1978 | United Kingdom . |
| 2040042 | 8/1980 | United Kingdom . |

*Primary Examiner*—Robert Raevis
*Attorney, Agent, or Firm*—Brumbaugh, Graves, Donohue & Raymond

[57] ABSTRACT

There is disclosed a method and apparatus for sampling gas from a hot dust-filled gas stream using a gas probe so arranged as to protrude into a gas- and dust-filled atmosphere, wherein the probe samples a gas portion of said gas stream, wherein the sample gas portion is sucked through the probe by a gas pump connected to the probe, and wherein at least a portion of the sample gas portion is first separated from suspended impurities and then fed to an analysis apparatus. The method and apparatus are further characterized in that the clogging or forming of bakings in the probe of dust suspended in the sample gas portion is prevented by activating said dust in the probe by means of a dust activation device comprising at least one of a laser emitter or means for deionization of the dust particles prior to filtration of the sample in the probe.

3 Claims, 4 Drawing Sheets

METHOD AND APPARATUS FOR SAMPLING GAS FROM A HOT DUST-FILLED GAS STREAM

The invention relates to a method and an apparatus for sampling gas from a hot, dust-filled gas stream, e.g. smoke gases from industrial plants, using a gas sampling probe, which gas samples are, after sampling, completely or partially fed to an analysis apparatus for further examination of the sample contents. The test result is generally used for regulating the operation of as well as the release of smoke gases from the relevant plant so as to obtain optimum operational conditions with due regard to the various environment regulations in force.

As such smoke gas samples are taken from a hot dust-filled gas stream wherein a temperature of up to about 1500° C. prevails, optionally higher, the gas sample will initially have approximately the same temperature thus making special demands to the probe for the treatment of such hot gases. It is a further problem with the sampling of the very hot gas sample that the dust particles therein tend to form bakings or deposits inside the probe so as to eventually clog it.

BACKGROUND OF THE INVENTION

According to the known technique such drawbacks have been countered e.g. by providing the probe with a special internal pipe or channel system through which a coolant, e.g. water, is circulated, and by letting the probe operate intermittently, i.e. by discontinuing the gas sampling at intervals in order to clean the probe interior, e.g. by blowing it out with compressed air. However, from a production and operation point of view a cooling system of the kind described results in a more complex and hence more vulnerable probe construction, and the requirement for cleaning means that the gas stream cannot be monitored unintermittently.

Examples of this prior art technique are disclosed in the following patent Nos. DE-A-1813877, DE-A-1815045, DE-A-3327180 and DK-B-162800.

Furthermore, German published patent application No. DE-A-2603948 discloses a gas sampling probe comprising a gas inlet section, a filter section and a gas outlet section and having suction and analysis units coupled thereto and which is not provided with a cooling device but works intermittently like the known probes referred to above because it is necessary to blow out the interior of the probe at intervals in order to remove undesired cloggings.

Lastly, German publication No. DE-B-2224955 and English patent application No. GB-A-2040042 discloses examples of electrically and mechanically operating devices for preventing dust cloggings in gas sampling probes. However, the device according to DE-B-2224955 does not establish an electrical field until after the dust-filled smoke gas has passed through the filter unit and therefore the field does not prevent dust cloggings in the filter proper, while the mechanical purification device according to GB-A-2040042 is a rotating rod arranged inside the probe pipe along the entire length thereof, and which thus permanently occupies a substantial part of the pipe section and restricts the gas passage through the pipe, and additionally the probe according to this latter citation is provided with a cooling system which is complex per se.

SUMMARY OF THE INVENTION

It is therefore the object of the present invention to provide a method and an apparatus which remedy the above-mentioned drawbacks of the prior art.

This object is achieved with a method of the kind described in claim 1 and an apparatus for carrying out the method and which is characterized by the subject-matter stated in the characterizing part of claim 2.

Additional advantageous features of the apparatus will appear from claims 3 through 7.

Thus, the particularly novel aspect of the method and the apparatus according to the invention is that the gas sampling is effected continuously by means of a gas sampling probe wherein no special coolant is employed and wherein the internal cleaning of the probe is effected continuously without interrupting the gas sampling and using the dust activation device incorporated in the probe which prevents bakings and cloggings of the hot dust particles contained in gas samples.

GENERAL DESCRIPTION OF THE DRAWING

The invention will now be explained in further detail with reference to the accompanying drawing which is a diagrammatical, sectional view of non-limiting embodiments of a probe according to the invention, and wherein FIG. 1 shows the probe with an electromagnetical dust activation device, FIG. 2 shows the probe with a purely mechanical dust activation device, FIG. 3 shows the probe with a dust activation device of the deionisation type, FIG. 3a is a sectional blown-up view of a detail of FIG. 3, and FIG. 4 is a particular embodiment of the embedding of the filter section of the probe.

In all of the figures identical reference numerals are used for identical parts of a probe.

DETAILED DESCRIPTION OF A PREFERRED EMBODIMENT

Figure 1:
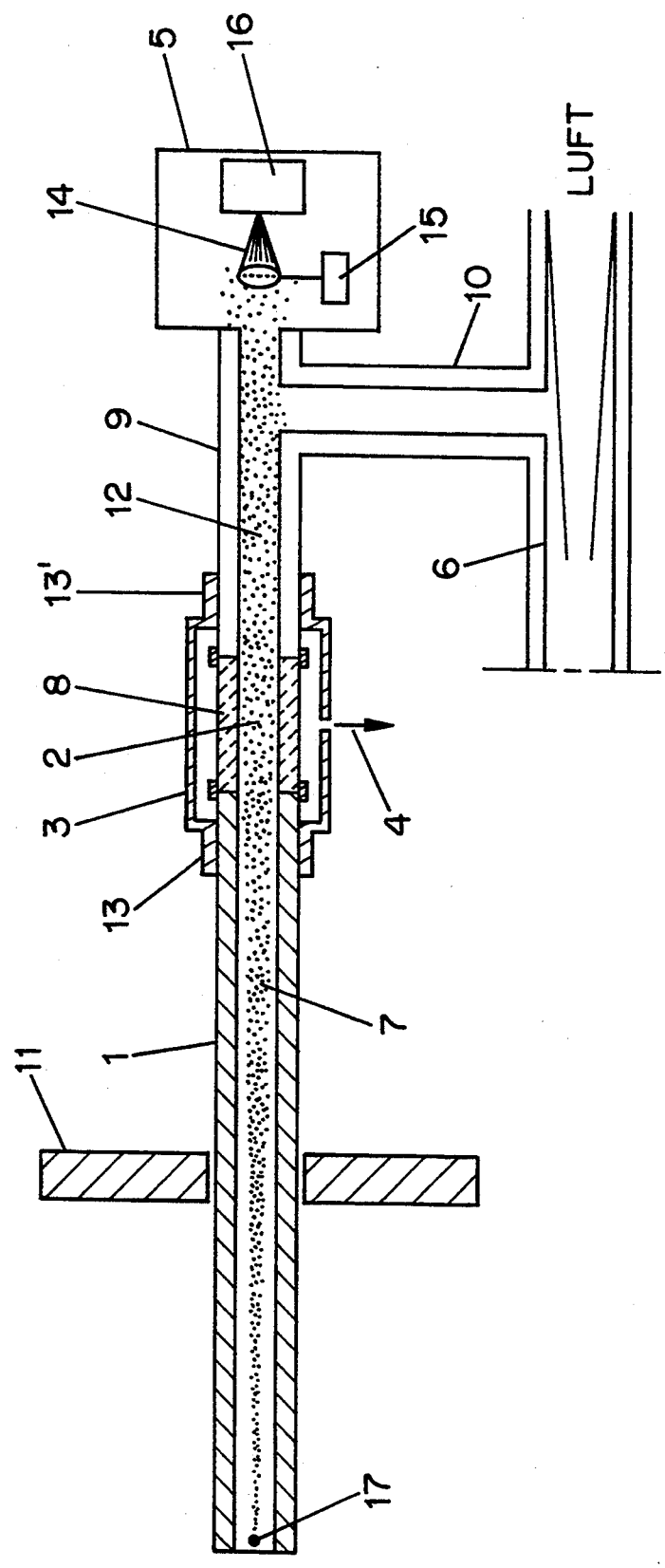

The basic components of the probe is constituted of three successively arranged pipe sections, all of which are made from a heat resistant material, viz. a gas inlet section 1, which protrudes into a hot dust-filled gas stream, e.g inside a smoke gas channel of which the wall facing the probe is denoted 11, a filter section 8 with pipe walls of a ceramic porous material, a gas outlet section 9 which through a gas conduit 10 is connected to a gas pump 6, e.g. an air pump which "draws" a gas sample out of the smoke gas channel and through the probe, and a filter housing 3, which in a gas-proof manner and by use of flanges 13,13' is connected to the adjacent ends of the gas inlet section 1 and the gas outlet section 9, respectively, and which surrounds the filter section 8. The filter housing 3 is provided with an outlet 4 for a sample gas portion purified of dust particles in the filter which sample is fed to an analysis apparatus (not shown) for further examination of the sample contents.

The smoke gas portion sampled from the smoke gas canal 11 with the probe is not only very hot, often about 1500° C. or more, it will also inherently contain a considerable amount of dust suspended in the gas sample. Such hot dust particles will have a propensity to clog in the internal probe areas 7, 2 and 12, the biggest risk of clogging occuring closest to the gas stream into which the probe protrudes and the clogging risk decreasing in the direction of movement of the sample gas portion through the probe.

In order to counter such clogging the probe is provided with a dust activation device which constantly keeps the dust particles flowing in the gas during its passage through the probe so that the dust particles are drawn out of the probe together with the gas portion leaving the same through the pump 6.

In FIG. 1 the dust activation device 5 is a dust activator which operates by means of electromagnetical radiant energy based on laser technique. The activator contains a laser emitter 16 whereto optics 14 are coupled which may be moved mechanically over a circle as well as to any side within the internal probe area 7, 2 and 12 by means of a guide and control mechanism 15. Over the entire internal length of the probe the laser energy emitted may be caused to focus in a predetermined focal point 17 in which the released energy is used to prevent clogging in the probe due to particle sedimentation.

Figure 2:
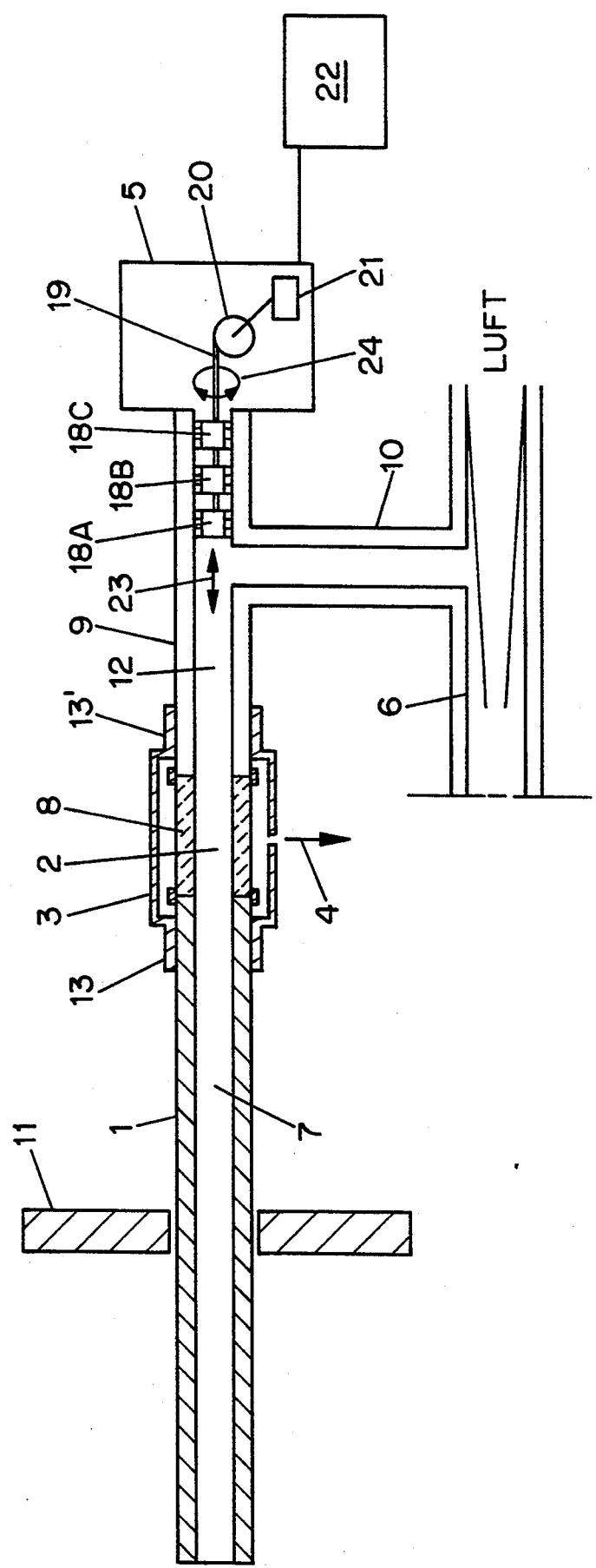
Figure 3:
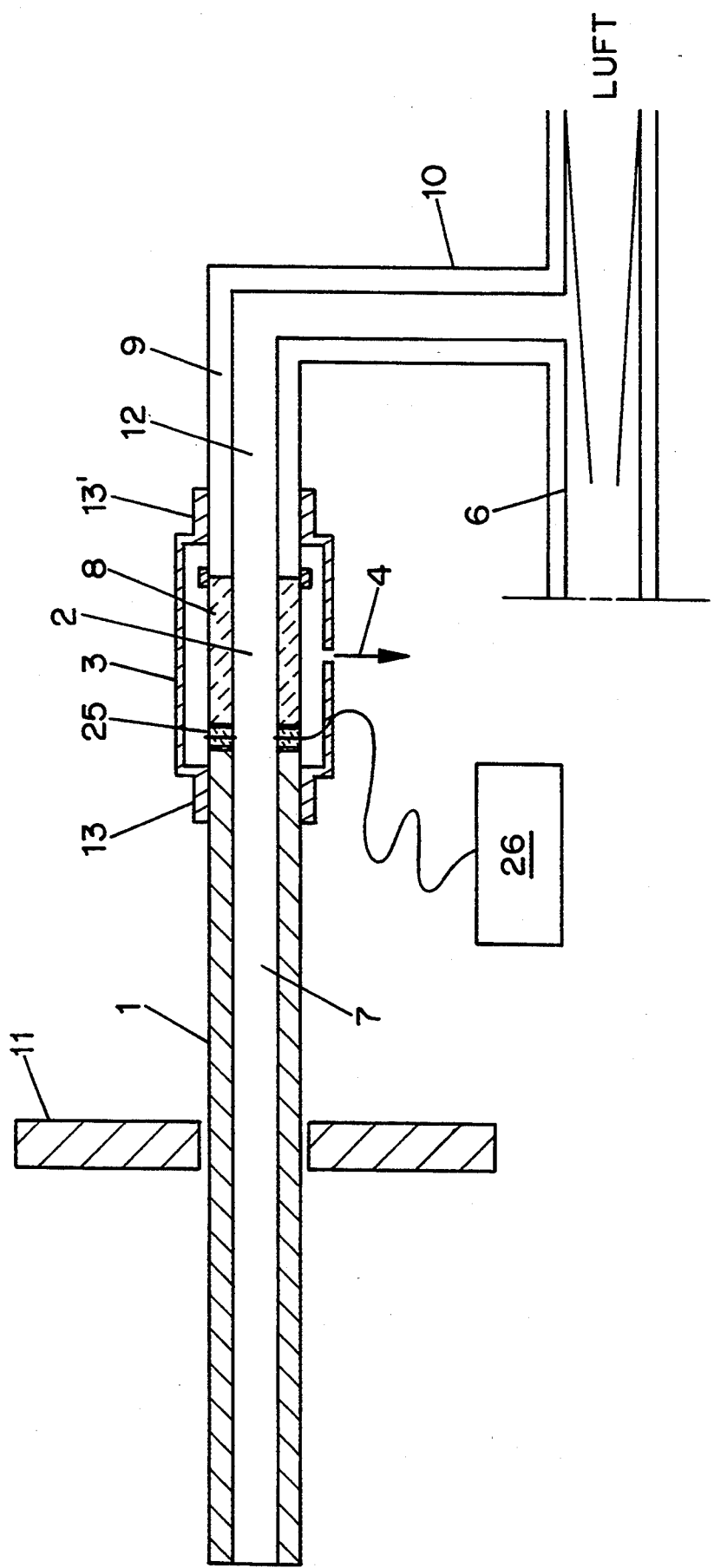
Figure 3A:
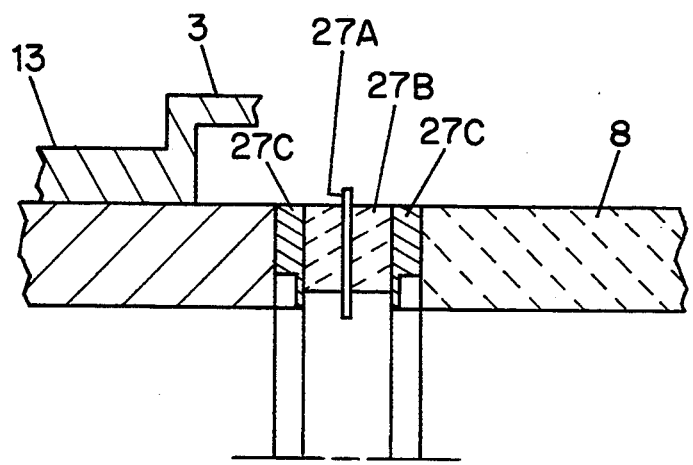
Figure 4:
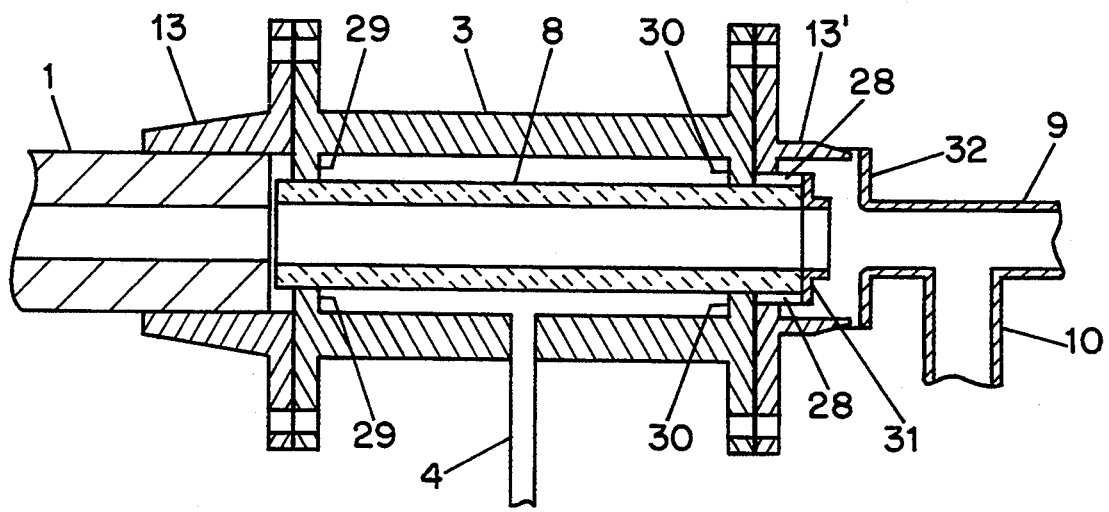

In the filter section 8 a sample gas portion is sampled after having been purified of dust particles by the filtration effect of the porous pipe walls, and is removed through the outlet 4. FIG. 2 shows a purely mechanically operating dust activation device 5 containing a dust activator which comprises three purification mandrels 18A, 18B and 18C which are adjustably arranged in the longitudinal direction of the probe and are rotatable around their axis on a common resilient shaft 19 which may be unwound or wound around a winding mechanism 20 which is activated by an actuator 21 and is controlled by a guide and control unit 22. The arrows 23 and 24 denote the movement direction of the mandrels 18A, 18B and 18C inside the probe. The purification mandrels have mutually different cleaning functions and cleaning degrees and along their external periphery they are coated or provided with a material which is resistant to the elevated temperatures and aggressive components of the gases contained in the probe.

The design of the individual mandrel provided with this material is such that in use the mandrel is caused to abut the corresponding section of the internal surface of the probe area thus providing an abrasive and cleaning effect. The mandrel 18 which is advanced most in the probe towards the hot dust-filled atmosphere from which the gas portion is sampled is coated on its surface with a very coarse cleaning material due to the intensive baking formation in this area. The mandrel 18B which is adjusted to move at a given distance behind the mandrel 18A between the latter and the filter section 8 is coated with a somewhat finer cleaning material, and the mandrel 18C which is adjusted to move within the filter section 8 proper is preferably provided with a cleaning material in the form steel brushes. Furthermore, all three mandrels are so designed that the gas flows essentially unimpeded through the probe with the mandrels in their respective cleaning positions.

The taking out of the sample gas portion from the filter section 8 through the outlet 4 of the filter housing 3 is effected as described above in connection with FIG. 1.

In the embodiment shown in FIG. 3 the dust activation in the probe is effected by means of a dust activator constructed as a deionisation system 25,26 for the dust particles contained in the gas. Between the gas inlet section 1 and the filter section 8 a metal ring 27C is inserted, preferably a ring of corrosion-resistant steel, the internal and external diameters of which correspond to the internal and external diameters of the gas inlet section 1 and the filter section 8, respectively. In the metal ring, cf. the section shown in FIG. 3*a*, along the ring periphery and at equal spaces a number of radial borings are made which each comprises an isolator 27B of e.g. a ceramic material. At the centre of each isolator and also in the radial direction of the ring an electrode 27A is mounted. The outwardly oriented ends of the electrodes 27A are coupled to the unit 26, which is a high-voltage supply of 4–5 kV, through an electricity conductive connection. The voltage supply unit 26 is earth connected to the metal ring 27C so as to form with an applied voltage an electrostatic field between the electrodes 27A and the relevant ring 27C. When the probe is in use this electrostatic field will be deformed to a certain extent by the gas flowing through the interior of the probe 7, 2 and 12 and the dust particles contained in the gas during its passage through the field will be deionised prior to the dust-filled gas being fed into the filter section 8 thereby avoiding that the dust particles are attracted to the surfaces of the internal probe area of opposite polarity and clogged on said surfaces thus ensuring that the particles remain suspended in the flowing gas which is sucked out by the pump 6. The deionisation therefore results in the internal area 2 in the filter section 8 being kept clean and permits unimpeded sampling through the outlet 4 of the filter housing 3 of a sample gas portion purified from dust particles.

As mentioned a gas sampling probe of the kind described above is used with gases having a very high temperature. As both the method and the probe according to the invention are characterized in the very feature that no coolant is used in connection with the gas sampling, the high temperatures may result in various movements caused by the coefficient of dilation of the gas inlet section 1, the filter section 8 and the gas outlet section 9, respectively, due to the mutually different material of which said sections are manufactured. To compensate for this the filter section 8 according to a particular embodiment of the probe may be displaceably embedded in the filter housing 3 as outlined in FIG. 4. Herein the filter section 8 rests in two annular guides 29,30 inside the housing 3 which guides may be cast integral with the housing. The flange 13' of the housing facing towards the gas outlet section 9 is at its end facing the filter section 8 connected to a flange-shaped securing ring 31 for the filter section 8 by means of a bellows 28 of corrosion-resistant steel which permits a dilation of the filter section 8 in the longitudinal probe direction the outlet section 9 forming the gas-proof connection to the filter housing flange 13' by means of a flange device 32 in such a manner that space is made for said dilation between the filter section 8 and the outlet section 9.

In order to avoid condensation inside the filter housing 3 when the probe is used during low outside temperatures a number of heating elements known per se may be mounted in the housing casing.

The invention is not limited to comprise the embodiments illustrated as examples above as mutually alternative solutions to a method and an apparatus for gas sampling without the use of a coolant, but comprises within the scope of the invention any combination of the mentioned embodiments for providing a purified sample gas portion for analysis purposes.

I claim:

1. A method for sampling gas from a hot dust-filled gas stream using a gas probe so arranged as to protrude into a gas- and dust-filled atmosphere, wherein the probe samples a gas portion of said stream, wherein the sample gas portion is sucked through the probe by a gas pump connected to the probe, and wherein at least a portion of the sample gas portion is first separated from suspended impurities and then fed to an analysis apparatus, said method further characterized by the step of preventing dust suspended in the sample gas portion from clogging or forming bakings in the probe by activating said dust in the probe by means of a dust activation device comprising at least a laser emitter.

2. A method according to claim 1, wherein the dust activation device comprises a combination of a laser emitter and a means for deionization.

3. A method according to claim 1, including the step of dust deactivation while maintaining the probe at the ambient temperature of the gas.

* * * * *